United States Patent [19]

McDonald

[11] Patent Number: 4,957,505
[45] Date of Patent: Sep. 18, 1990

[54] CANNULATED SPRING FORCEPS FOR INTRA-OCULAR LENS IMPLANTATION METHOD

[76] Inventor: Henry H. McDonald, 65 N. Madison, Suite 810, Pasadena, Calif. 91101

[21] Appl. No.: 431,332

[22] Filed: Nov. 3, 1989

[51] Int. Cl.⁵ .......................... A61F 2/16; A61F 9/00; A61B 17/00
[52] U.S. Cl. ...................................... 623/6; 606/107; 606/206
[58] Field of Search ............... 623/6; 606/1, 107, 205, 606/206, 210, 211

[56] References Cited

U.S. PATENT DOCUMENTS

| | | |
|---|---|---|
| 1,837,277 | 12/1931 | Lund . |
| 3,980,086 | 9/1976 | Kletschka et al. . |
| 4,573,998 | 3/1986 | Mazzocco ................................ 623/6 |
| 4,759,359 | 7/1988 | Willis et al. .......................... 606/107 |
| 4,785,810 | 11/1988 | Baccala et al. ...................... 623/6 X |
| 4,813,957 | 3/1989 | McDonald ............................... 623/6 |
| 4,834,094 | 5/1989 | Patton et al. ........................ 606/107 |
| 4,836,202 | 6/1989 | Krasner ................................ 606/107 |

FOREIGN PATENT DOCUMENTS

| | | |
|---|---|---|
| 361627 | 10/1922 | Fed. Rep. of Germany . |
| 2555952 | 6/1985 | France . |
| 119055 | 9/1918 | United Kingdom . |

Primary Examiner—Ronald Frinks
Attorney, Agent, or Firm—William W. Haefliger

[57] ABSTRACT

Intraocular implantation of a folded lens and haptics is carried out using a forceps with blades and a cannula, the forceps interacting with the cannula to maneuver this implantation.

11 Claims, 2 Drawing Sheets

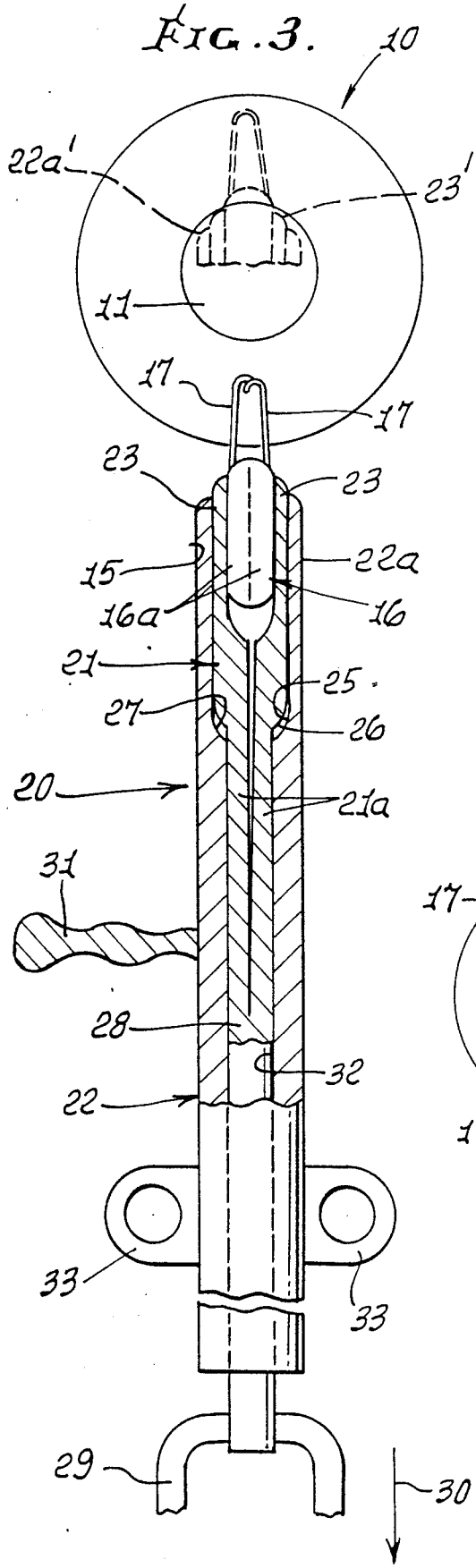
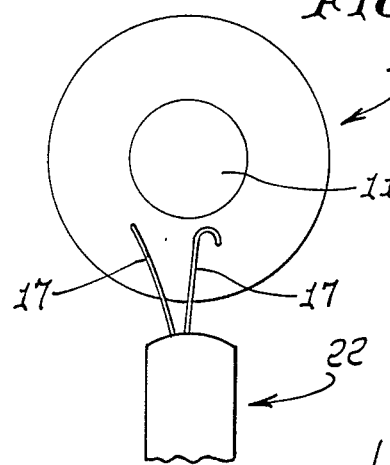
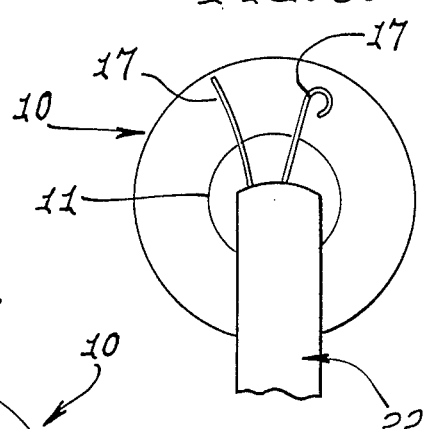
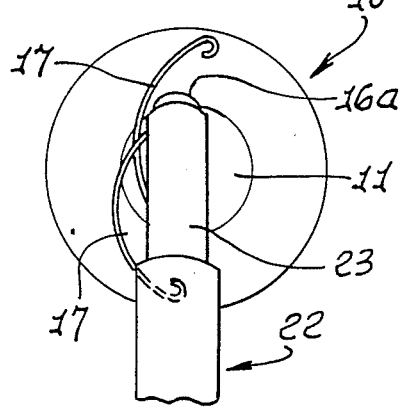
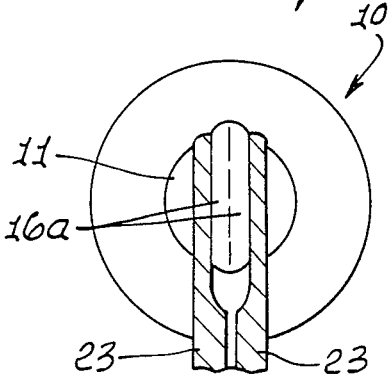

4,957,505

CANNULATED SPRING FORCEPS FOR INTRA-OCULAR LENS IMPLANTATION METHOD

BACKGROUND OF THE INVENTION

This invention relates generally to intraocular lens implantation, and more particularly concerns apparatus and method for achieving such implantation via a very small surgical incision in the corneo-scleral limbus of the eye.

In the past, forceps have been used with blades that clamp the plastic lens for introducing it into the eye via a relatively wide wound or incision in the corneoscleral limbus. A typical wound was required to have a width of about 7-15 millimeters in order to pass the forcep blades and to allow spreading of the blades to release the plastic lens in the eye.

Problems encountered included laceration of the elastic silicone lens, and undesirable sudden release and rapid unfolding of the lens (as opposed to gentle release) causing injury to intraocular tissue, due to inability to separate the blades widely and gently. The usual wide incision is undesirable due to the amount of suturing required to close the wound, and time required for such suturing, increased or undesirably long convalescence time, increase in astigmatic complications, difficulty in preventing collapse of the intraocular chambers during the operation, and increased risk of post-operative complications. Further, plastic lenses could and did at times become captured by the blades of prior forceps, requiring dangerous instrumentation to release the lens from the grasp of such forceps.

SUMMARY OF THE INVENTION

It is a major object of the invention to provide method and apparatus, overcoming the above problems and difficulties. Basically the invention permits wide separation of the blades and gentle release of the folded lens within the eye, while motion is transmitted to the blades via a very narrow incision.

The method involves implanting a plastic lens into the eye zone from which a natural but cataractous lens has just been removed (or removed in the past) as via a narrow surgical incision in the corneo-scleral limbus, and while using a forceps received in a cannula, the forceps having blades projecting beyond arm portions, and the blades clamping the plastic (artificial) lens which has haptic loops attached thereto. The method includes the steps:

(a) receiving said arm portions and folded lens in the cannula to position the folded lens in the forward end of the cannula, with the haptic loops in predetermined positions relative to the folded lens, and to the cannula, (b) introducing said forward end of the cannula into the eye via said incision and into proximity to said lens zone, (c) relatively displacing the cannula and said forceps to controllably retract the forward end of the cannula relative to the blades and folded lens, thereby allowing the haptic loops to move away from the folded lens and toward walls defined by the lens capsule, (d) continuing said relative displacement of the cannula and forceps to effect relative separation of the blades, thereby accommodating unfolding release of the folded lens in the capsule whereby the haptic loops then position the unfolded lens in the lens zone in the capsule, (e) continuing said relative displacement of the cannula and forceps to effect movement of the blades relatively toward one another, (f) and retracting the cannula and forceps from the eye, via said incision.

The forward end of the cannula may typically and advantageously define an internal pocket in which the blades and folded lens are positioned during said (b) step, and said (c) and (d) steps are effected to cause the blades and folded lens to move relatively forwardly and outwardly and outwardly relative to said pocket. The cannula and forceps typically have interengageable cam surfaces, and said (e) step is carried out to effect interengagement of said cam surfaces to cause the blades to move toward one another as the blades are moved into the pocket.

Apparatus employing the invention typically includes (a) a surgical forceps having two elongated arms and two blades, each blade integral with an arm at the forward end thereof, (b) and an elongated cannula within which the arms and blades are received with the plastic lens held in folded condition by and between the blades, (c) whereby the forward end of the cannula may be introduced into the eye via said incision to position the folded lens and loops in proximity with said eye lens zone, (d) and whereby the cannula and forceps may be relatively displaced to controllably relatively retract the forward end of the cannula relative to the blades and folded lens, thereby allowing unfolding release of the folded lens in the eye lens zone and movement of the haptic loops in said zone to position the unfolded plastic lens therein.

These and other objects and advantages of the invention, as well as the details of an illustrative embodiment, will be more fully understood from the following specification and drawings, in which:

DRAWING DESCRIPTION

FIG. 3 is an elevation showing details of an instrument, including forceps and cannula, used to implant the FIG. 2 lens in the capsule shown in FIG. 1;

FIGS. 4-8 are similar diagrammatic views showing stages during lens implantation.

DETAILED DESCRIPTION

Figure 1:
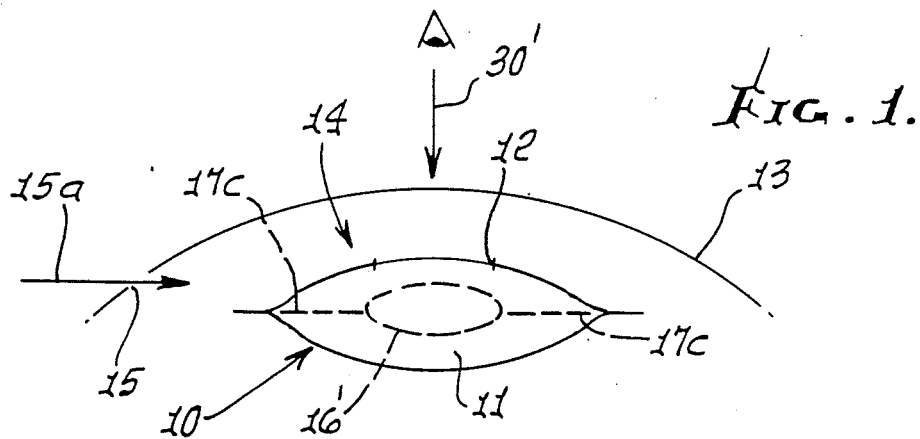
FIG. 1 is a section taken through an eye showing the location of an eye lens capsule from which cataract occuluded natural lens material has been removed.

In FIG. 1, a lens capsule 10 is shown after removal of cataractus material from the interior lens zone 11, the material removed for example via a cut-away at 12 (from which a flap has been removed, by eye surgery). The outer boundary of the eye appears at 13, and aqueous material is normally located at 14 between the capsule and the eye boundary. A small incision is made at 15 in the eye corneoscleral tissue to permit insertion of surgical instruments, that incision being small, as for example less than about 3.5 mm. See arrow 15a indicating the direction of instrument insertion.

Figure 2:
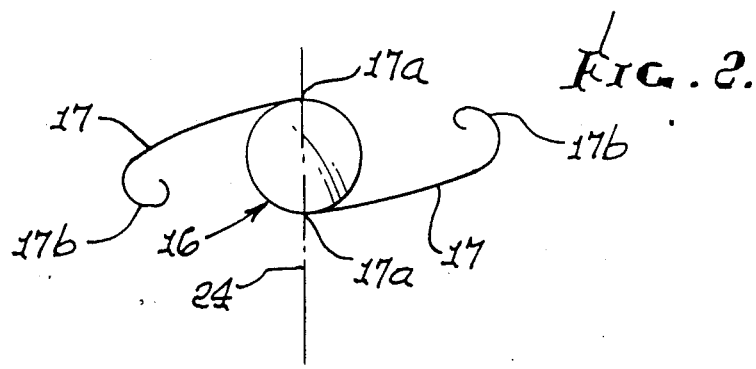
FIG. 2 is a plan view of an artificial lens, such as a foldable plastic lens, with haptics in the form of looping arms ("loops")

FIG. 2 shows a molded plastic (artificial) lens 16 to be implanted in the capsule 10, as at location 16' in FIG. 1, shown in broken lines. Haptic loops (arms) 17 are integral with the lens at opposed lens boundary locations 17a, and they are "springy" to be resiliently foldable close to the lens, and to spring outwardly when released so that their turned loop portions 17b locate themselves at the interior periphery of the capsule (see location 17c) to thereby position the lens centrally of the capsule as at 16' in FIG. 1. The present invention is concerned with instrumentation and techniques (method) to controllably insert the lens 16 and its haptics into the capsule, using a minimum length incision 15, as referred to.

Referring now to FIG. 3, surgical apparatus appears at 20, and basically includes a forceps 21, that grasps the lens to be implanted, and a cannula (hollow tube) 22 for containing the forceps and to allow forceps relative movement lengthwise in the cannula. The cannula forward end portion 22a is of a width to be insertable through the minimum incision 15 to position the forceps blades 23, and grasped lens 16 in the lens reception zone 11, for lens release. As seen in FIG. 3, the lens 16 is folded, as along diametral axis 24 shown in FIG. 2, so that the lens halves 16a folded together, are grasped by and between the two blades, in position to be released for unfolding when the blades subsequently spread apart. Note the pocket 25 formed in the cannula to receive the spreadable arm portions 21a of the forceps. The latter have convex surfaces or shoulders 26 that bulge outwardly for camming action to be described; and shoulders 26 are receivable near or at the bottom of the pocket, formed by correspondingly concave shoulders 27 of the cannula. Shoulders 27 may act as stop shoulder to limit axial retraction of the forceps relative to the cannula. Note in this regard, that the forceps plunger 28 mounting the spreadable arms 21a may be manually retracted by pulling a ring 29 in rearward direction 30, while lateral handle 31 on the cannula is grasped. Bore 32 in the cannula receives plunger 28, and intersects pocket 25, the pocket being laterally enlarged relative to the bore. Other means to advance and retract the plunger, controllably, may be provided (springs, for example). Rings 33 may be mounted on the cannula, for finger reception. FIG. 3 also shows, in broken lines, the forwardmost extent of cannula forward end insertion, at 22a', into the eye zone 11. Associated forwardmost extent of blade insertion appears at 23'.

FIGS. 4-9 show stages of folded plastic lens insertion and manipulation, using the forceps and cannula, as described and as viewed downwardly in arrow direction 30 in FIG. 1, by the surgeon. In FIG. 4, the lens haptics 17, projecting forwardly, are being inserted into the zone 11, via slit 15 and the boundary of zone 11. FIG. 5 shows the cannula approximately fully inserted, the haptic loops spreading outwardly. In FIG. 6 the cannula is being retracted, while the forceps remain in forward position to locate the lens in centered relation, in zone 11. Note in FIGS. 4-6, the folded lens halves extend in planes substantially parallel to the plane of the capsule (normal to arrow 30 in FIG. 1). FIG. 5 shows the cannula entering the capsule via opening 11.

Figure 8:
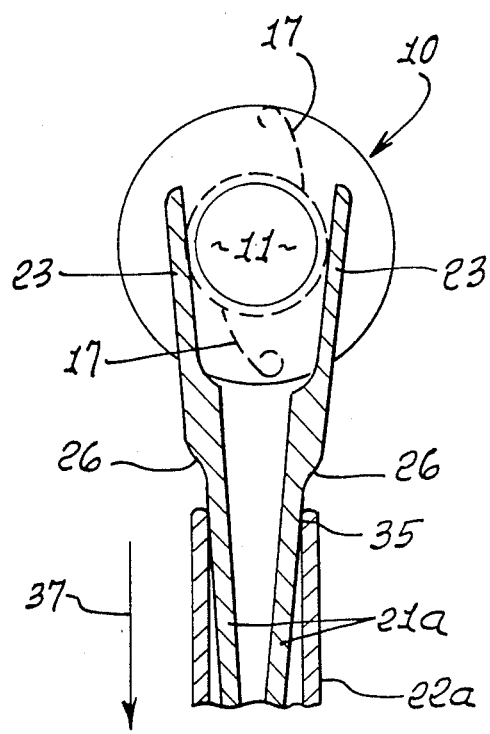

In FIG. 7 the cannula and forceps are rotated approximately 90° about the length axis of the cannula, to orient the planes of the folded lens halves normal to the plane of the pancake shaped capsule. Thus, as the lens subsequently unfolds, the lens halves will expand into a plane parallel to the plane of the capsule. FIG. 8 shows the forceps arms separated (to release the lens for unfolding). This can be accomplished by retracting the cannula relative to the arms 23 of the forceps, which spring outwardly due to their yieldably outwardly biased resiliency. The extent of arm spreading, to control lens release, is controlled by engagement of the arms, as at 35, with forward edges of the cannula, which in turn is controlled by relative axial positioning of the forceps plunger 28 and the cannula 22.

Figure 9:
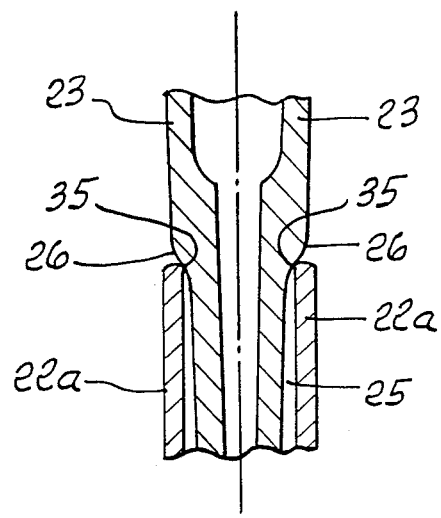
FIG. 9 is a fragmentary view showing forceps blade retraction effected by forceps arm camming against cannula surfaces.

After the lens has expanded and has been adjusted by the blades to assure proper positioning of the haptics 17, the blades are retracted in direction 37, in FIG. 8. FIG. 9 shows the blades 23 being closed together due to camming engagement of convex surfaces 26 against the cannula forward edges at 35, as the forceps is retracted endwise relative to the cannula. Thereafter, the cannula forward extent, and blades fully received in pocket 25, are retracted from the eye, via narrow incision 15.

I claim:

1. The method of intraocular implantation of a plastic lens in the eye lens zone within a lens capsule from which a natural lens has been removed, and via a surgical incision in the corneo-scleral limbus, the method employing a surgical forceps having blades projecting beyond arm portions, the blades clamping the plastic lens which has haptic loops attached thereto, the method also employing an elongated cannula, including:

(a) receiving said arm portions and folded lens in the cannula to position the folded lens in the forward end of the cannula, with the haptic loops in predetermined positions relative to the folded lens, and to the cannula, (b) introducing said forward end of the cannula into the eye via said incision and into proximity to said lens zone, (c) relatively displacing the cannula and said forceps to controllably retract the forward end of the cannula relative to the blades and folded lens, thereby allowing the haptic loops to move away from the folded lens and toward walls defined by the lens capsule, (d) continuing said relative displacement of the cannula and forceps to effect relative separation of the blades, thereby accommodating unfolding release of the folded lens in the capsule whereby the haptic loops then position the unfolded lens in the lens zone in the capsule, (e) continuing said relative displacement of the cannula and forceps to effect movement of the blades relatively toward one another, (f) and retracting the cannula and forceps from the eye, via said incision.

2. The method of claim 1 wherein said (e) step includes effecting relative retraction of the blades into the forward end of the cannula and pocketing the blades therein.

3. The method of claim 1 wherein the forward end of the cannula defines an internal pocket in which the blades and folded lens are positioned during said (b) step, and said (c) and (d) steps are effected to cause the blades and folded lens to move relatively forwardly and outwardly relative to said pocket.

4. The method of claim 3 wherein said (e) step is carried out to effect movement of the blades into said pocket.

5. The method of claim 4 wherein the cannula and forceps arm portions have interengageable cam surfaces, and said (e) step is carried out to effect interengagement of said cam surfaces to cause the blades to move toward one another as the blades are moved into the pocket.

6. The method of claim 1 including producing said incision in the corneo-scleral limbus, to have an overall length less than about 3.5 mm.

7. The method of claim 1 wherein said capsule defines a first plane and the folded lens defines lens halves which define second planes which are oriented to extend generally parallel to said first plane during said (b) step.

8. The method of claim 7 including rotating the blades in the capsule to orient the folded lens second planes to extend generally normal to said first plane, prior to said (d) step.

9. The method of claim 1 including moving the blades in the capsule in conjunction with said (c) step to center the folded lens in the capsule, prior to said (d) step.

10. Surgical apparatus useful for eye surgery wherein an incision is made in the eye corneoscleral tissue, and via which a plastic lens is to be introduced into an eye lens in a capsule from which a natural lens has been removed, the lens having haptic loops attached thereto, the combination comprising
   (a) a surgical forceps having two elongated arms and two blades, each blade integral with an arm at the forward end thereof,
   (b) and an elongated cannula within which the arms and blades are received with the plastic lens held in folded condition by and between the blades,
   (c) whereby the forward end of the cannula may be introduced into the eye via said incision to position the folded lens and loops in proximity with said eye lens zone,
   (d) and whereby the cannula and forceps may be relatively displaced to controllably relatively retract the forward end of the cannula relative to the blades and folded lens, thereby allowing unfolding release of the folded lens in the eye zone and movement of the haptic loops in said zone to position the unfolded plastic lens therein.

11. The apparatus of claim 10 wherein the cannula forward end forms a pocket that receives the blades as the blades and folded lens are introduced into the capsule.

* * * * *